United States Patent [19]

Badertscher et al.

[11] Patent Number: 5,116,575
[45] Date of Patent: May 26, 1992

[54] POWDERED ANTI-MICROBIAL COMPOSITION

[75] Inventors: Duncan C. Badertscher, Cleveland; Raymond C. Kralovic, Austinburg, both of Ohio

[73] Assignee: Steris Corporation, Mentor, Ohio

[21] Appl. No.: 342,189

[22] Filed: Apr. 24, 1989

Related U.S. Application Data

[63] Continuation-in-part of Ser. No. 229,917, Aug. 8, 1988, which is a continuation-in-part of Ser. No. 140,388, Jan. 4, 1988, Pat. No. 4,892,706, and a continuation-in-part of Ser. No. 165,189, Mar. 7, 1988, Pat. No. 5,037,623, which is a continuation-in-part of Ser. No. 826,730, Feb. 6, 1986, Pat. No. 4,731,222.

[51] Int. Cl.$^5$ .............................. A61L 2/18
[52] U.S. Cl. ........................ 422/28; 422/16; 422/292; 422/293
[58] Field of Search ............ 422/16, 28, 292, 293

[56] References Cited

U.S. PATENT DOCUMENTS

| 4,051,058 | 9/1977 | Böwing et al. |
| 4,051,059 | 9/1977 | Bowing et al. |
| 4,115,060 | 9/1978 | Finley et al. |
| 4,120,652 | 10/1978 | Scholer et al. |
| 4,547,381 | 10/1985 | Mason et al. ............... 426/316 |
| 4,826,658 | 5/1989 | Kay ........................... 422/30 |
| 4,892,706 | 1/1990 | Kralovic et al. ........... 422/28 |
| 4,938,262 | 7/1990 | Williams et al. ........... 422/28 X |

FOREIGN PATENT DOCUMENTS

| 0232170 | 8/1987 | European Pat. Off. |
| 0332310 | 9/1989 | European Pat. Off. |
| 0357238 | 3/1990 | European Pat. Off. |
| 2229426 | 12/1974 | France |
| 1566671 | 5/1980 | United Kingdom |

OTHER PUBLICATIONS

Sporkenbach et al., ZBL. Bakt. Hyg., I. Abt. Orig. B173, 1981, pp. 425–439.
Baldry, et al., "Peroxygen Disinfectants", *Specialty Chemicals*, Nov. 1983.
Greenspan, et al., J. Organic Chem., vol. 20, No. 2, Feb. 1955, pp. 215–217.
Mücke, "Properties of Peracetic Acid", Wissenschaftliche Zeitschrift der Universität Rostock, Mathematisch-Naturwissenschaftliche Reihe, 19(3), 1970, pp. 267–270.
Eggensperger, "Disinfectants Based on Peracid-Releasing Compounds", Zbl. Bakt. Hyg., I. Abt. Orig. B 168, 1979, pp. 517–524.

*Primary Examiner*—Jill A. Johnston
*Attorney, Agent, or Firm*—Fay, Sharpe, Beall, Fagan, Minnich & McKee

[57] ABSTRACT

Medical instruments, which may include brass, copper, aluminum, stainless steel, carbon steel, or plastic parts are microbially decontaminated (sterilized or disinfected) in an antimicrobial solution. To provide a long shelf life, premeasured doses of powdered reagents are sealed in an ampule until ready for use. The powdered reagents are selected such that they react in the presence of water to form a strong oxidant solution in an appropriate concentration to be effective as an antimicrobial. The preferred powdered reagents include acetylsalicylic acid and sodium perborate which react in the presence of water to form a peracetic acid solution. Moreover, these dry reagents form sodium metaborate and salicylic acid, both corrosion inhibitors to inhibit corrosion of metal parts of the medical instruments. The ampule may also hold a preselected dose of phosphate or other water soluble corrosion inhibitors and a wetting agent.

19 Claims, 2 Drawing Sheets

POWDERED ANTI-MICROBIAL COMPOSITION

BACKGROUND OF THE INVENTION

This application is a continuation-in-part of U.S. application Ser. No. 229,917, filed Aug. 8, 1988, which is a continuation-in-part of U.S. application Ser. No. 140,388, filed Jan. 4, 1988, now U.S. Pat. No. 4,892,706 and Ser. No. 165,189, filed Mar. 7, 1988, now U.S. Pat. No. 5,037,623 which in turn are continuations-in-part of application Ser. No. 826,730, filed Feb. 6, 1986, now U.S. Pat. No. 4,731,222.

The present invention relates to anti-microbial agents. It finds particular application in conjunction with automated sterilizing or disinfecting of medical instruments and will be described with particular reference thereto. However, it is to be appreciated that the present invention will find utility in sterilizing and disinfecting a wide range of objects, either automatically or manually.

Heretofore, most medical instruments have been sterilized in a steam autoclave. In hospitals and large facilities, medical instruments and equipment were transported to a central sterilizing facility where they were sterilized under the supervision of sterilizing room technicians. In a steam autoclave, the equipment was subject to superheated steam at high pressures, depressurized, and cooled. One of the drawbacks of the steam autoclave is that many medical instruments cannot withstand the high temperatures and pressures. Another drawback resides in the one to two hour cycle time.

Instruments and equipment which could not withstand the pressure or temperature of the autoclave were commonly sterilized with ethylene oxide gas. The equipment was sealed in a sterilizing chamber which was pressurized with the ethylene oxide gas. After an appropriate sterilizing cycle, the equipment was degassed for twelve to sixteen hours in a vacuum or about 72 hours in ambient atmospheric conditions to remove the highly toxic ethylene oxide. One of the drawbacks to ethylene oxide sterilization resided in the long cycle times. Another drawback resided in the need for training technicians to handle the highly toxic ethylene oxide gas systems. Yet another drawback was that some medical equipment could not be sterilized with ethylene oxide gas.

Liquid sterilization systems were utilized for equipment which would not withstand the high temperatures of steam sterilization or were too expensive to use only once per day as is necessitated by the long sterilizing times of ethylene oxide sterilization. The equipment was immersed in a vat or tank that had been filled with a sterilizing solution, such as stabilized hydrogen peroxide or glutaraldehyde. Because such liquid sterilizations were normally performed manually, the skill and care of the technician were controlling factors in whether sterilization or disinfection were, in fact, attained. In many instances, the technician was required to mix the components of the anti-microbial composition. Even when mixed properly, relatively long immersion times on the order of six to ten hours were commonly required to assure sterilization. Moreover, many liquid sterilization systems were highly corrosive to metal parts, particularly brass, copper, and aluminum. With long immersion times, even brass and stainless steel could be pitted and sharp cutting edges dulled.

Peracetic acid is one of the most potent organic peroxide biocides. Peracetic acid is available in a liquid form as an equilibrium mixture with acetic acid and hydrogen peroxide. Peracetic acid is limited in its usefulness as a chemical sterilant for medical devices because it has a very low pH and is very corrosive to metals, e.g. carbon, steel, and brass, even in dilute solutions. Buffers and anticorrosive agents must be added to protect the steel and brass parts of medical instruments. However, relatively large amounts of buffering and anticorrosive agents must be employed, due not only to the low pH and acidity of the peracetic acid equilibrium mixture, but also to neutralize the effects of the biologically inert acetic acid and hydrogen peroxide. The peracetic acid and hydrogen peroxide in the equilibrium mixture tend to degrade slowly, liberating gaseous oxygen. In order to prevent gas pressure from accumulating in the containers holding the peracetic acid mixture, a venting system must be provided. The venting systems tend to vent not only oxygen, but also very corrosive and highly pungent vapors which must be neutralized by special packaging.

In the bleaching art, dry compositions have been mixed with an activator compound to release a peroxy bleaching substance. Typically, an inorganic peroxide or other hydrogen peroxide releasing agent is intermixed with an activator compound. Of the dozen or so classes of activator compounds, N,N,N',N'-tetraacetylethylene diamine (TAED) and tetraacetylglycouracil (TAGU) are most common. These activator compounds are large organic molecules with limited solubility in water. With the acid precursor compounds, having relatively low water solubilities, only small concentrations of peracetic acid can be produced. Moreover, the undissolved solids of the precursor and activator compounds become temporarily suspended in the solution and can deposit in and block small channels of immersed equipment.

In accordance with the present invention, a new and improved dry antimicrobial composition is provided which overcomes the above referenced problems and others.

SUMMARY OF THE INVENTION

In accordance with the present invention, a method of sterilizing is provided. Powdered reagents are mixed with a stable liquid to produce a strong oxidant and buffer solution. Items to be sterilized are immersed in the solution until sterilized.

In accordance with a more limited aspect of the present invention, the powdered reagents include a water soluble acid precursor and a water soluble peroxy compound and the stable liquid includes water.

In accordance with a yet more limited aspect of the present invention, the acid precursor includes acetylsalicylic acid and the persalt includes sodium perborate in appropriate concentrations to produce a peracetic acid solution in a concentration of 0.2% w/v.

In accordance with another aspect of the present invention, a premeasured sealed vial of antimicrobial concentrate is provided. The vial contains a water soluble acid precursor and a water soluble peroxy compound which, when mixed with water, produce a strong oxidant peracetic acid and buffer solution.

In accordance with a more limited aspect of the present invention, the acid precursor is a acetylsalicylic acid and the peracid is sodium perborate which results in a peracetic acid peroxy compound and buffer solution.

One advantage of the present invention is that it is stable during shipping and handling. No special venting is required.

Another advantage of the present invention is that it provides an anti-microbial agent which quickly sterilizes or disinfects medical equipment or the like.

Another advantage of the present invention is that it works on substantially all materials with minimal corrosion.

Yet another advantage of the present invention is that it facilitates automated sterilizing and minimizes the opportunity for operator error.

Still further advantages of the present invention will become apparent upon reading and understanding the following detailed description.

BRIEF DESCRIPTION OF THE DRAWINGS

The invention may take form in various components and arrangements of components or in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
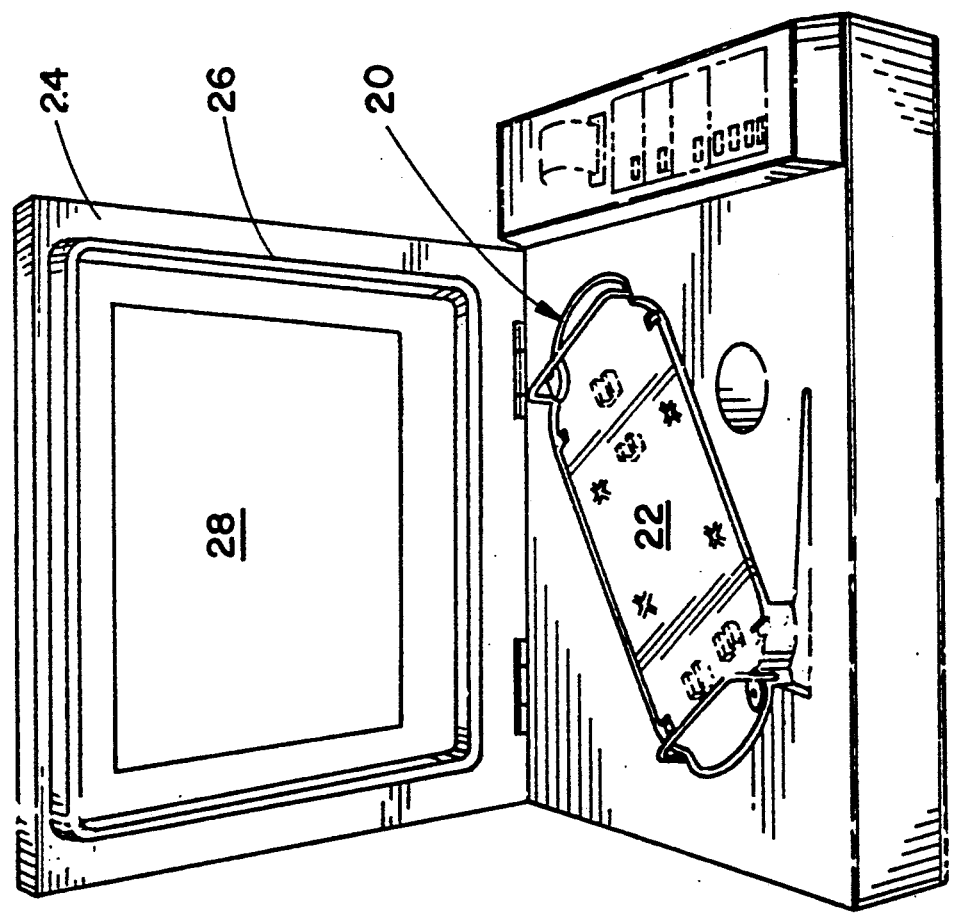
FIG. 1 is a perspective view of a sterilizing apparatus in accordance with the present invention; and, FIG. 2 is a tubing diagram of the sterilizer of FIG. 1.
Figure 2:
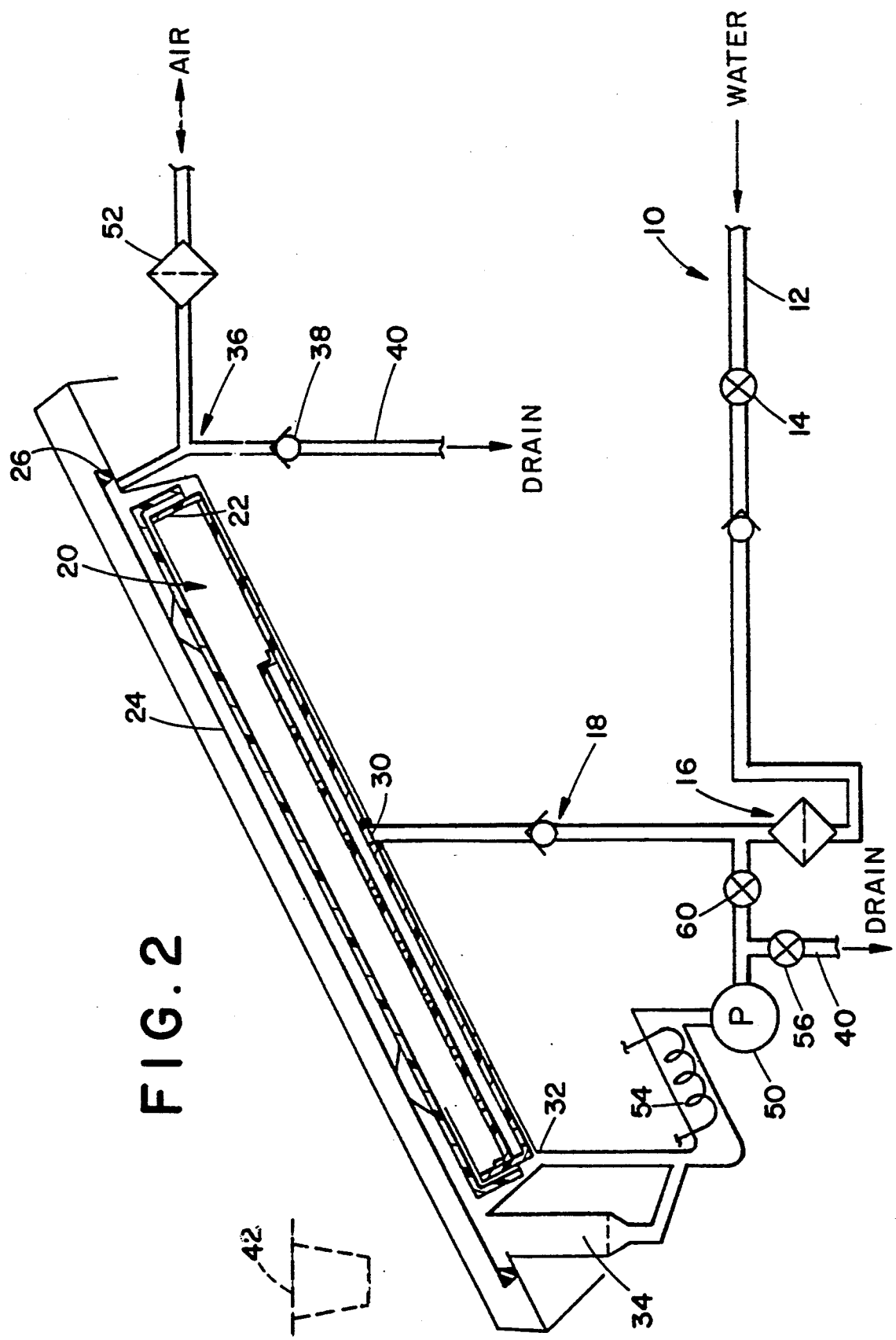

With reference to FIGS. 1 and 2, a dilutant or water source 10 supplies water or other fluid reagents. In the preferred sterilizer embodiment, the water source includes a length of tubing 12 connected with a water spigot or other building plumbing and a control valve 14 for selectively preventing and permitting the flow of water to a sterilizing means 16. In the preferred embodiment, the sterilizing means is a filter which removes particles which are as large or larger than bacteria. Thermal, chemical, radiological, and other conventional water sterilizing means are also contemplated. Optionally, an in-line water treatment means may be provided for modifying the chemical composition of the water. For example, a water softening cartridge may be provided for reducing or eliminating calcium and magnesium salts from the water. Alternately, various water treatments may be added to the water, such as a wetting agent, a sequestering agent, or others of the reagents to be discussed herein below.

A tubing system 18 connects the filter or other sterilizing means 16 with a basin or other means 20 for receiving an item to be sterilized. In the preferred embodiment, the basin receives a removable container or tray 22 configured in accordance with the item to be sterilized, e.g. an endoscope. The container may have appropriate liquid ports, vents, sterilant distribution system, medical instrument positioners and retainers, closures, etc. such that instruments can be sterilized, rinsed, and stored within the container without opening the container. A lid 24 is sealed to the basin in a lowered position by a resilient gasket 26. Optionally, a transparent window 28 is defined in the lid.

The tubing system 18 includes a basin inlet 30 for filling the basin to surround the items with a sterilant solution and a basin drain 32. A reagent receiving well 34 collects the fluid from the filled basin. Vent lines 36 enable air to be vented from the container and basin such that they are completely filled with the sterilant solution, rinse water, or other liquids. Any excess fluid is discharged through check valve 38 into a drain line 40.

A sealed ampule 42 with a premeasured dose of dry ingredients that form corrosion inhibitors and anti-microbial agents when mixed with water is emptied into the well 34. Optionally, two compartments may be provided such that the corrosion inhibitors are introduced and circulated first over the item to be sterilized or disinfected. This provides corrosion protection before the corrosive anti-microbial agent contacts the item. In the preferred embodiment, the corrosion inhibitors and anti-microbial agent reach the item contemporaneously. As described in greater detail below, the powdered water-soluble reagents include compositions when mixed with water or a water-based solution, form a strong oxidant or other antimicrobial agent. The reagents further provide buffers and anticorrosive agents. More specifically to the preferred embodiment, the dry ingredients include a water-soluble acid precursor and a water-soluble persalt which, when dissolved in water, form a peracetic acid solution with an anti-microbially effective concentration of peracetic acid. Moreover, the water soluble acid precursor and water soluble peracid react or are mixed with other ingredients to provide a buffer, e.g. a borate, for bringing the pH to a neutral level and to inhibit steel corrosion. Other corrosion inhibitors, such as a molybdate for inhibiting aluminum and steel corrosion, a triazole for inhibiting copper and brass corrosion, and the like are optionally included in the powdered ingredients. Wetting and sequestering agents may also be included in the dry ingredients.

The operator closes the lid 24 and the system is filled with water. A pump 50 selectively draws solution or water from the basin 20 through well 34 and returns it to the basin inlet 30. The water dissolves the powdered reagents allowing them to react, forming the antimicrobial solution. Preferably, the vent line 36 is very short and of a substantial diameter such that the solution is circulated over exposed surfaces of the drain check valve 38 and an air sterilizing filter 52. A heating coil 54 adjusts the temperature of the solution. Recirculation continues until the interior of the medical items and all exposed surfaces of the tubing system, pump, basin, container, and valves are sterilized. Alternately, once fully dissolved and distributed the sterilant may remain quiescent without further circulation for a selected duration.

After the preselected sterilization or disinfecting period, the antimicrobial solution is drained through a drain valve 56. Sterile air is drawn into the system through the air sterilizing filter 52 that removes any particles the size of a bacteria or larger. The fill valve 14 is opened and the drain valve 56 is closed such that the sterile filter 16 provides a source of sterile rinse. Note that the sterile rinse liquid flows only in contact with sterilized surfaces of the tubing system and valves in order to assure sterility. Every tubing and valve surface from the filter 16 to the drain has been exposed to the circulating antimicrobial solution for a sufficient duration to assure that it is microbial contamination-free. The pump 50 circulates the sterile rinse through the system for a selected duration sufficient to rinse any deposits or residue, such as salts, that strong buffered solutions tend to deposit. At the end of the rinse cycle, the rinse solution is drained by opening the drain valve 56. When a return valve 60 is closed, the pump 50 pumps liquid from the system out the drain valve 56. Additional drain lines (not shown) and aspirators or pumps (not shown) may be provided for removing liquids from every region of the system. The exact location of such additional drains will be dependent on the bends and contours of the plumbing system.

In the preferred embodiment, the ampule contains acetylsalicylic acid (acid precursor) and sodium perborate (persalt). The relative amounts of these two additives are selected so as to produce the chemical reaction:

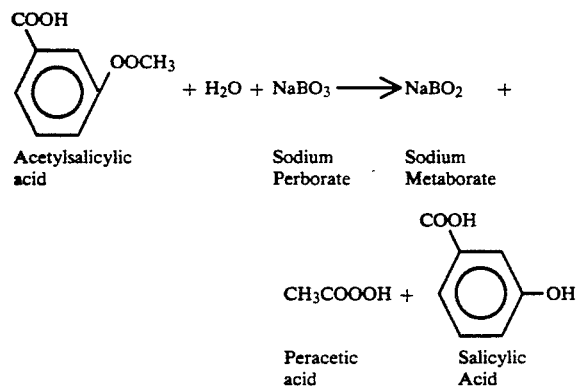

Acetylsalicylic acid    Sodium Perborate    Sodium Metaborate

Peracetic acid    Salicylic Acid

The total volume of dry ingredients is such that the resultant water solution has a concentration of peracetic acid of 0.2% w/v — a biocidally effective concentration. The Sodium Metaborate ($NaBO_2$) is an inorganic corrosion inhibitor and the Salicylic acid is an organic corrosion inhibitor with a benzoate function. Preferably, an additional powdered water-soluble phosphate is also present in the ampule to provide additional corrosion resistance when dissolved by the water. The chemical formulation of the phosphate is preferably selected such that it is inert relative to the above described chemical reaction, or at least does not interfere with the chemical reactions formation of peracetic acid and corrosion inhibitors.

A 0.2% w/v peracetic acid solution and associated corrosion inhibitors generated by the above chemical reaction is anti-microbially effective with twelve minutes exposure at 50° C. even to *Clostridium sporgenes* inoculum on a penicylinders carrier, the carrier and inoculum most resistant to peroxyacetic acid. Antimicrobial test results are summarized in Table 1 below in which each test was conducted at 50° C. with twelve minutes exposure and the peracetic acid at 0.2% w/v.

TABLE 1

| | Efficacy Data | | | |
|---|---|---|---|---|
| Spore Inoculum | Carrier | Tested | Sterile | Unsterile |
| *Clostridium sporgenes* | Penicylinders | 130 | 130 | 0 |
| | +5% Horse Serum* | 5 | 5 | 0 |
| *Clostridium sprogenes* | Suture Loops | 30 | 30 | 0 |
| | +5% Horse Serum* | 5 | 5 | 0 |
| *Bacillus subtilis* | Penicylinders | 20 | 20 | 0 |
| | +5% Horse Serum* | 5 | 5 | 0 |
| *Bacillus subtilis* | Suture Loops | 20 | 20 | 0 |
| | +5% Horse Serum* | 5 | 5 | 0 |
| | | 220 | 220 | 0 |

*5% horse serum was added before the addition of the carriers

Other oxidizing or antimicrobial agents can also be generated in situ, such as chlorine dioxide, chlorine, hydrogen peroxide, and mixtures thereof. More specifically, potassium chromates, sodium chloride, and phosphates may be mixed according to the following equation to produce a strong chlorine oxidant on the addition of water:

$$K_2Cr_2O_7+6\ NACl+7\ H_3PO_4\Delta 4\ K_2HPO_4+Cr_2N(HPO_4)_3+HOCl+6H_+ +H_2O$$

Optionally, excess dichromate and an organic corrosion inhibitor may be provided for improved buffering and corrosion inhibiting.

Hydrogen peroxide and an inorganic inhibitor can be generated:

$$NaBO_3+H_2O+H_3PO_4\rightarrow H_2O_2+NaBO_2+H_3PO_4$$

Similarly, chlorine dioxide can be generated from powdered ingredients on the addition of water:

$$2NaClO_2+LiClO+H_2O\rightarrow 2ClO_2+NaOH+NaCl+LiOH$$

A mixed biocide system can be achieved by adding sodium chloride to the peracetic acid reaction to produce ;) hypochlorous acid.

$$CH_3COOOH+Na^++Cl^-\rightarrow CH_3COONa+HOCl$$

Excess peracetic acid is deliberately present such that both peracetic acid and hypochlorous acid are present in the biocidal solution.

In these compositions, it is preferable to add additional corrosion inhibitors and buffers to protect copper, brass, aluminum, steel, and the like. Preferably, corrosion inhibitors are added which result in three corrosion inhibitors in the final solution. One is an organic inhibitor, one is an inorganic inhibitor, and the third can be either.

The copper and brass corrosion inhibitors are preferably benzotriazoles and tolytriazoles, which are preferred due to their stability in the presence of strong oxidizing compounds. Mercaptobenzathiozol might also be utilized but is more apt to be oxidized or destabilized by strong oxidizers.

Azoles, benzoates, and other five membered ring compounds may also prove acceptable as copper and brass corrosion inhibitors.

By way of example, the anti-corrosive buffering compounds may include a mixture of phosphate in sufficient volume to produce a final concentration of 1.25% weight per Volume and molybdates in an appropriate amount to produce a final solution of 0.011% weight per volume. Phosphates may also be effective in the range of 0.2% to 12% and the molybdates may be effective from 0.1 to 10%. Optionally, chromates, dichromates, tungstates, vanadates, other borates, and combinations thereof, may be substituted in appropriate concentrations to inhibit steel corrosion, i.e. buffer to a generally neutral pH, and aluminum corrosion.

In hard water, the phosphates tend to cause calcium and magnesium salts to precipitate and coat the instruments being sterilized and parts of the sterilizing system. A sequestering agent appropriate to prevent precipitation, such as sodium hexametaphosphate, may be provided. Of course, if deionized or soft water is utilized the sequestering agent may be eliminated. However, to insure universal applicability with any water that might be utilized, the presence of a sequestering agent is preferred.

A wetting agent present from 0.001 to 1.0% (w/v) improves the wetting of the surface of the instrument by the anti-microbial agent. The wetting agent has also been found to increase penetration of the anti-microbials improving anti-microbial efficacy while reducing corrosion.

The following are examples that illustrate the corrosion inhibiting effectiveness of various strong oxidant anti-microbial formulations. Coupons of 410 stainless steel, brass (ASTM B36-C 2600), aluminum (5052-H 32), and carbon steel scalpel blades were exposed to two changes of sterilant mix for a total of four hours exposure at 50-55° C. One set of coupons was run in distilled water and a sterilant mix (0.5% sodium perborate and 0.5% aspirin) and a second set in tap water and sterilant mix. A second set of tests was performed using brass and aluminum coupons, and carbon steel scalpel blades in a matrix with concentrations of disodium phosphate of 0, 0.2, 0.4, 0.5, and 0.7% and concentrations of benzotriazole of 0, 0.001, 0.005, 0.01, and 0.02%. Each type of coupons were exposed to sterilant mix and additives for three hours at 50-55° C. All coupons were rinsed well with distilled water and acetone and allowed to dry before evaluation.

Corrosion or discoloration was noted on all materials using just the basic peracetic acid, sodium metaborate, and salicylic acid solution. Carbon steel and 410 stainless steel showed only minor corrosion. Aluminum was discolored and showed some pitting. Brass was heavily corroded on most surfaces and showed some pitting. In the matrix, the addition of 0.001% benzotriazole or 0.4% phosphate eliminated corrosion on carbon steel. The addition of 0.4% phosphate eliminated corrosion on aluminum. For brass, the addition of 0.2% phosphate or 0.05% benzotriazole eliminated pitting corrosion. However, phosphate caused darkening of brass which was apparent unless 0.02% benzotriazole was added. Random spotting of brass occurred at all concentrations. This sort of corrosion can be eliminated by adding a surfactant.

The invention has been described with reference to the preferred embodiments. Obviously, modifications and alterations will occur to others upon reading and understanding the preceding detailed description. It is intended that the invention be construed as including all such alterations and modification insofar as they come within the scope of the appended claims or the equivalents thereof.

Having thus described the preferred embodiments, the invention is now claimed to be:

1. A method of microbially decontaminating items, the method comprising:
   measuring selected quantities of powdered ingredients, which powdered ingredients include:
   a powdered borate, and
   a powdered water soluble acid precurser, which reacts in water to form a oxidant of sufficient strength to kill at least pathogenic microorganisms, an organic corrosion inhibitor, and a borate corrosion inhibitor;
   sealing the powdered ingredients in an ampule until an item is to be microbially decontaminated;
   opening the ampule and dissolving and reacting the powdered ingredients in a water containing liquid to form an anti-microbially effective solution of the oxidant, the borate corrosion inhibitor, and the organic corrosion inhibitor;
   immersing the item in the solution at least until pathogenic microorganisms are killed; and,
   rinsing the item.

2. A method of microbially decontaminating items, the method comprising:
   measuring selected quantities of dry reagents, which dry reagents includes an acetylsalicylic acid precursor and a sodium perborate peracid,
   sealing the dry ingredients in an ampule until an item is to be microbially decontaminated;
   opening the ampule and dissolving the dry reagents in a water containing liquid such that an anti-microbially effective solution of a peracetic acid and a borate and salicylic acid corrosion inhibitor are formed;
   immersing the item in the solution for a duration sufficient to kill at least pathogenic microbes; and,
   rinsing the item.

3. The method as set forth in claim 2 wherein the acetylsalicylic acid and sodium perborate are present in appropriate proportions tot eh water such that a chemical reaction in accordance with:

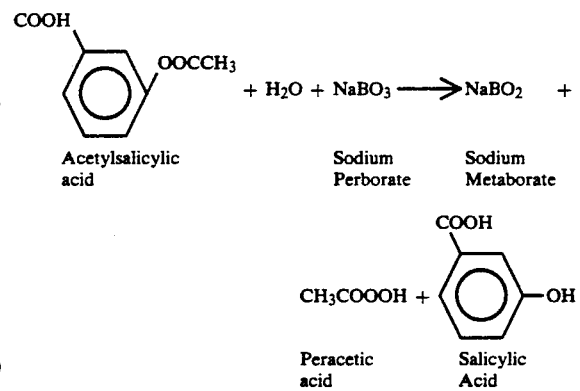

occurs and the resultant solution has at least a 0.02% w/v concentration of peracetic acid.

4. A method of sterilizing items, the method comprising:
   measuring selected quantities of powdered, which the powder ingredients include a mixture of at least one of:
   $K_2Cr_2O_7$, NaCl, and $H_3PO_4$;
   $NaBO_3$ and $H_3PO_4$; and
   $NaClO_2$ and LiClO; and
   acetylsalicylic acid and a perborate;
   sealing the powdered ingredients in an ampule;
   opening the ampule and reacting the powdered ingredients in a water containing solution such that an anti-microbially effective solution of an oxidant which kills microorganisms and a inorganic corrosion inhibitor if formed;
   immersing the item in the solution for a sufficient duration to kill microorganisms on the item; and,
   rinsing the item.

5. A method of disinfecting items, the method comprising:
   measuring selected quantities of powdered ingredients, the powdered ingredients including a mixture of an acetylsalicylic acid precursor and at least one of (i) $NaBO_3$, (ii) $NaBP_3$ and NaCl, and (iii) a powdered salt that forms an inorganic corrosion inhibitor when the mixture reacts in water;

sealing the powdered ingredients in an ampule until an item is to be disinfected;

opening the ampule and reacting the powdered ingredients in a liquid such that an anti-microbially effective solution of a peracetic acid oxidant, an inorganic corrosion inhibitor, and a salicylic organic corrosion inhibitor are formed;

immersing the item in the solution until disinfected; and, rinsing the item.

6. A method of microbially decontaminating items, the method comprising:

measuring selected quantities of powdered ingredients which form an oxidant that kills at least pathogenic microorganisms when mixed with a dissolving liquid and at least one corrosion inhibitor from the class consisting essentially of:
benzotriazoles, tolytriazoles, mercaptobensathiozol, azoles, bensoate, molybdates, phosphates, chromates, dichromates, tungstate, vanadate, and borate;

sealing the powdered ingredients in an ampule until an item is to be microbially decontaminated;

opening the ampule and dissolving the powdered ingredients in the dissolving liquid such that an anti-microbially effective solution of the pathogenic microorganism killing oxidant and corrosion inhibitors is formed;

immersing the item in the solution at lest until the pathogenic microorgansism are killed; and, rinsing the item.

7. A method of microbially decontaminating items, the method comprising:

measuring selected quantities of powdered ingredients which dissolve and react to form an oxidant which is sufficiently strong to kill at least pathogenic microorganisms and at least one organic corrosion inhibitor from the class consisting essentially of:
benzotriazoles, tolytriazoles, mercaptobenzathiozol, azoles, imidazoles, thiozoles, indoles, pyrazoles, and benzoate;

and at least on inorganic corrosion inhibitor from the class consisting essentially of:
molybdates, phosphates, chromates, dichromates, tungstate, silicates, vanadate, and borate;

sealing the powdered ingredients in an ampule;

opening the ampule and dissolving the powdered ingredients and reacting the dissolved ingredients to form an anti-microbially effective solution of the pathogenic microorganism killing oxidant and corrosion inhibitors;

immersing the item in the solution until the pathogenic microorganisms are killed; and, rinsing the item.

8. The method as set forth in claim 7 wherein the powdered ingredients further include a water soluble acid precursor and a water soluble peroxy compound.

9. A method of sterilizing items, the method comprising:

measuring selected quantities of powdered reagents which form a strong oxidant which is effective to kill microorganisms when dissolved;

sealing the powdered reagents in an ampule;

disposing the item to be sterilized in a closed basin;

opening the ampule, dissolving the powdered ingredients, and reacting the dissolved ingredients to form a sterilant solution, the dissolving and reacting steps including recirculating the sterilant solution from a drain end of the basin through interconnecting tubing and back to a basin inlet until microorganisms on the item, in the basin, and in the interconnecting tubing are killed, whereby the interconnecting tubing is sterilized with the item; and rinsing the item.

10. The method as set forth in claim 9 wherein the rinsing step further includes passing a sterile rinse liquid from a source of the sterile rinse liquid through the sterilized interconnecting tubing such that the sterile rinse liquid passes only in contact with surfaces that were sterilized by the sterilizing solution, whereby the sterile rinse liquid is prevented from carrying microbial contamination to the sterilized item.

11. The method as set forth in claim 10 wherein the item is a medical instrument.

12. A method of microbially decontaminating medical instruments, the method comprising:

dissolving and reacting powdered acetylsalicylic acid and a powdered perborate in water to form a peracetic acid solution of at least 0.001% w/v of peracetic acid, a borate corrosion inhibitor, and a salicylic organic corrosion inhibitor;

immersing the medical instrument in the peracetic acid, borate corrosion inhibitor, and salicylic organic corrosion inhibitor solution until at least pathogenic microorganisms are killed.

13. A microbial decontamination apparatus comprising:

a receiving region for receiving dry reagents which react in water to form a microorganism killing oxidant solution;

a plurality of disposable ampules, each ampule holding a preselected dose of the dry reagents to be emptied into the reagent receiving region;

interconnecting tubing for interconnecting the dry reagent receiving region with a pump, a basin for receiving an item to be microbially decontaminated, and a water supply, such that water from the water supply selectively flows through and dissolves the dry reagents in the reagent receiving region forming the microorganism killing oxidant solution and such that the pump selectively pumps the microorganism killing solution through the interconnecting tubing into the basin.

14. The apparatus as set forth in claim 13 further including a sterilizing means operatively connected with the water supply for sterilizing water supplied to the interconnecting tubing and a drain for selectively draining liquid from the interconnecting tubing such that the tubing selectively directs a sterile rinse liquid through the basin to rinse a microbially decontaminated item.

15. The apparatus as set forth in claim 14 wherein the powdered reagents include a water soluble acid precursor and a water soluble peracid.

16. The apparatus as set forth in claim 15 wherein the acid precursor is acetylsalicylic acid and the peracid is sodium perborate such that the strong oxidant is peracetic acid.

17. A microbial decontamination apparatus comprising:

a plurality of disposable ampules, each ampule having a preselected dose of powdered reagents including a mixture of at least one of:
(i) $K_2Cr_2O_7$, NaCl, and $H_3PO_4$ powders,
(ii) $NaBO_3$ and $H_3PO_4$ powders,
(iii) $NaClO_2$ and LiClO powders, (iv) acetylsalicylic acid precursor and borate peracid powders;

a receiving region for receiving the powdered reagents and reacting the powdered reagents with water to form an oxidant and corrosion inhibitor solution;

interconnecting tubing for interconnecting the powdered reagent receiving region with a pump, a basin for receiving an item to be microbially decontaminated, and a water supply, such that water from the water supply selectively flows through and reacts the powdered reagents in the reagent receiving region forming the oxidant and corrosion inhibitor solution and such that the pump selectively pumps the oxidant and corrosion inhibitor solution through the interconnecting tubing into the basin microbially decontaminating the interconnecting tubing and the item.

18. The apparatus as set forth in claim 17 wherein the powdered reagents further include at least one corrosion inhibitor selected from the group consisting of:
benzotriazoles, tolytriazoles, mercaptobenzathiozol, axoles, imidazoles, thiozoles, indoles, pyrazoles, benzoate, molybdates, phosphates, chromates, dichromates, tungstate, silicates, vanadate, and borate.

19. An ampule for supplying a premeasured dose of powdered reagents to sterilize an item in one cycle of an automated sterilizing apparatus, the ampule containing acetylsalicylic acid powder and a borate powder such that when the powdered reagents are mixed with water, they react to form a corrosion inhibiting antimicrobial solution of peracetic acid antimicrobial agent and a borate inorganic corrosion inhibitor, and a salicylic acid corrosion inhibitor in the water.

* * * * *

UNITED STATES PATENT AND TRADEMARK OFFICE
CERTIFICATE OF CORRECTION

PATENT NO. : 5,116,575
DATED : May 26, 1992
INVENTOR(S) : Badertscher, et al.

It is certified that error appears in the above-indentified patent and that said Letters Patent is hereby corrected as shown below:

In column 5, line 15 and in claim 3,

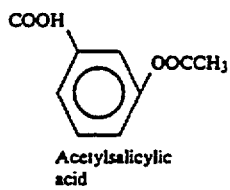

should read:

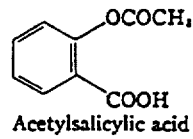

In column 5, line 22 and in claim 3,

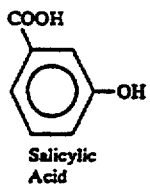

should read:

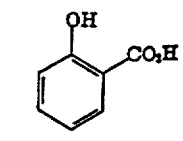

Signed and Sealed this

Thirteenth Day of September, 1994

Attest:

BRUCE LEHMAN

Attesting Officer

Commissioner of Patents and Trademarks